United States Patent
Vincent et al.

(10) Patent No.: US 10,283,784 B2
(45) Date of Patent: May 7, 2019

(54) FUEL CELL FOR DETECTING A POLLUTANT

(71) Applicant: COMMISSARIAT A L'ENERGIE ATOMIQUE ET AUX ENERGIES ALTERNATIVES, Paris (FR)

(72) Inventors: Remi Vincent, Grenoble (FR); Sebastien Rosini, Grenoble (FR); Denis Tremblay, Pommiers-la-Placette (FR)

(73) Assignee: COMMISSARIAT À L'ÉNERGIE ATOMIQUE ET AUX ÉNERGIES ALTERNATIVES, Paris (FR)

(*) Notice: Subject to any disclaimer, the term of this patent is extended or adjusted under 35 U.S.C. 154(b) by 159 days.

(21) Appl. No.: 15/512,219

(22) PCT Filed: Sep. 15, 2015

(86) PCT No.: PCT/FR2015/052471
§ 371 (c)(1),
(2) Date: Mar. 17, 2017

(87) PCT Pub. No.: WO2016/042257
PCT Pub. Date: Mar. 24, 2016

(65) Prior Publication Data
US 2017/0279129 A1    Sep. 28, 2017

(30) Foreign Application Priority Data
Sep. 19, 2014 (FR) ...................... 14 58846

(51) Int. Cl.
*H01M 8/0273* (2016.01)
*H01M 8/0276* (2016.01)
(Continued)

(52) U.S. Cl.
CPC .......... *H01M 8/0202* (2013.01); *G01N 27/42* (2013.01); *H01M 8/02* (2013.01);
(Continued)

(58) Field of Classification Search
None
See application file for complete search history.

(56) References Cited

U.S. PATENT DOCUMENTS 6,210,820 B1    4/2001    Knights et al.
6,214,487 B1 *  4/2001    Kelley ................... H01M 8/02
                                                 429/430
(Continued)

FOREIGN PATENT DOCUMENTS

EP          1 017 121 A2    7/2000

OTHER PUBLICATIONS

International Search Report dated Dec. 22, 2015 in PCT/FR2015/052471 filed Sep. 15, 2015.

*Primary Examiner* — Yoshitoshi Takeuchi
(74) *Attorney, Agent, or Firm* — Oblon, McClelland, Maier & Neustadt, L.L.P.

(57) ABSTRACT

A fuel cell including: a diaphragm/electrodes assembly including a first electrode forming an anode, and a first reinforcement attached to a surface of the diaphragm and surrounding the first electrode; two bipolar plates, having the diaphragm/electrodes assembly placed therebetween and including at least one flow collector passing therethrough, a first surface of the diaphragm including an active area and a connection area and arranged between the flow collector and the active area; a conductor track rigidly connected to the first surface of the diaphragm and extending between the connection area and one edge of the diaphragm that projects beyond the first reinforcement; and a measurement electrode, positioned on the connection area of the first surface of the diaphragm and making electrical contact with the conductor track.

15 Claims, 5 Drawing Sheets

(51) Int. Cl.
*H01M 8/0271* (2016.01)
*H01M 8/04* (2016.01)
*H01M 8/04298* (2016.01)
*H01M 8/04313* (2016.01)
*H01M 8/04694* (2016.01)
*H01M 8/0202* (2016.01)
*H01M 8/02* (2016.01)
*H01M 8/0258* (2016.01)
*G01N 27/42* (2006.01)
*H01M 8/0256* (2016.01)
*H01M 8/0267* (2016.01)
*H01M 8/04089* (2016.01)

(52) U.S. Cl.
CPC ....... *H01M 8/0256* (2013.01); *H01M 8/0258* (2013.01); *H01M 8/0267* (2013.01); *H01M 8/0269* (2013.01); *H01M 8/0273* (2013.01); *H01M 8/04089* (2013.01)

(56) References Cited

U.S. PATENT DOCUMENTS

2001/0028966 A1 10/2001 Knights et al.
2008/0299422 A1 12/2008 Perry et al.

\* cited by examiner

FUEL CELL FOR DETECTING A POLLUTANT

The invention relates to fuel cell stacks including a stack of electrochemical cells and, more particularly, a stack including bipolar plates and proton exchange membranes.

Fuel cell stacks are in particular envisaged as a power source for automotive vehicles manufactured on a large scale in the future or as an auxiliary power source in aeronautics. A fuel cell stack is an electrochemical device that directly converts chemical energy to electrical energy. A fuel cell stack comprises a stack of multiple cells in series. Each cell typically generates a voltage of the order of 1 volt, and their stacking allows a higher supply voltage to be generated, for example of the order of a few hundred volts.

Among the known types of fuel cell stacks, mention may be made in particular of proton exchange membrane (PEM) fuel cell stacks operating at low temperature. The compactness of such fuel cell stacks is particularly advantageous. Each cell comprises an electrolytic membrane that allows only protons to pass through while excluding electrons. The membrane comprises an anode on a first face and a cathode on a second face in order to form a membrane/electrode assembly (MEA).

At the anode, dihydrogen used as fuel is ionized in order to produce protons which pass through the membrane. The membrane thus forms an ionic conductor. The electrons produced by this reaction migrate toward a flow plate, then pass through an electrical circuit outside the cell in order to form an electric current. At the cathode, oxygen is reduced and reacts with the protons in order to form water.

The fuel cell stack may comprise multiple plates, referred to as bipolar plates, for example made of metal, stacked on top of one another. The membrane is positioned between two bipolar plates. The bipolar plates may comprise flow apertures and channels for continuously guiding the reactants and the products toward/away from the membrane. The bipolar plates also comprise flow channels for guiding cooling liquid that removes the heat generated. The reaction products and unreactive species are removed by being carried along by the flow until reaching the output of the flow channel networks. The flow channels of the various flows are separated by bipolar plates in particular.

The bipolar plates are also electrically conductive in order to collect electrons produced at the anode. Another function of the bipolar plates is to mechanically transmit stack clamping stresses, which are necessary for the quality of the electrical contact. Gas diffusion layers are interposed between the electrodes and the bipolar plates and make contact with the bipolar plates.

Electronic conduction is achieved through the bipolar plates, and ionic conduction is obtained through the membrane.

Certain bipolar plate designs use homogenization zones to connect input and output manifolds to the various flow channels of the bipolar plates. The reactants are brought into contact with the electrodes via input manifolds and the products are removed via output manifolds which are connected to the various flow channels. The input manifolds and the output manifolds generally pass all the way through the thickness of the stack. The input and output manifold are usually obtained by:
respective apertures passing through each bipolar plate at its periphery;
respective apertures passing through each membrane at its periphery;
joints, each interposed between a bipolar plate and a membrane.

Various technical solutions are known for bringing the input and output manifolds into communication with the various flow channels. It is known practice in particular to form passages between two metal sheets of a bipolar plate. These passages terminate on one side in respective manifolds apertures and, on the other side, in injection apertures. A homogenization zone comprises channels that bring injection apertures into communication with flow channels.

The homogenization zone comprises in general: a cooling fluid transfer zone, an oxidizer circuit homogenization zone and a fuel circuit homogenization zone which are superposed and lead to a cooling liquid manifold, an oxidizer circuit manifold and a fuel circuit manifold, respectively.

The fluid flowing through the fuel cell stacks may be subject to pollutants which may affect operation. For example, fuel cells are subject to a risk of corrosion of carbon-based elements which results in the formation of carbon monoxide. Carbon monoxide mixes with the dihydrogen of the fuel and poisons the anode through adsorption. Dinitrogen may mix with the dihydrogen and thus dilute it, thereby affecting the performance of the fuel cell stack. The air used as an oxidizer may also include a non-negligible quantity of pollutants which may poison the cathode through adsorption.

It is known practice to implement operating cycles intended to remove certain pollutants. It is thus known practice to implement dihydrogen purges for the purpose of preventing the dihydrogen from being overly diluted by dinitrogen. However, no satisfactory means exist that allow a pollutant to be precisely identified or quantified for the purpose of triggering such operating cycles, in particular for a stack of cells of a fuel cell stack intended for commercial distribution.

The document U.S. Pat. No. 6,214,487 describes a fuel cell stack incorporating a measurement capacitor formed in the reactive zone of a membrane/electrode assembly. A capacitor plate is in particular formed by delimiting an insulating separator isolating it with respect to a surrounding electrode. Forming capacitor plates in the active zone negatively affects the performance of the fuel cell stack and makes its connections difficult to produce. This document also does not allow the streams of reactants toward the active zone to be homogenized.

The document EP1017121 describes a fuel cell stack having an electrochemical cell equipped with a membrane/electrode assembly. This electrochemical cell is dedicated to detecting a pollutant and is brought into communication with the fuel flow. In this electrochemical cell, the anode of the membrane/electrode assembly forms a reactive zone used as a pollution sensor. This fuel cell stack sacrifices one electricity-generating electrochemical cell. Moreover, the measurement of pollution in the dedicated cell is not representative of the conditions in the rest of the electrochemical cells of the stack.

The document US 2008/0299422 describes a fuel cell stack having an electrochemical cell equipped with a membrane/electrode assembly. This electrochemical cell is dedicated to detecting pollution and is brought into communication with the hydrogen flow. Here, the hydrogen is forced through the membrane. Depending on the quantity of hydrogen passing through the membrane, it is possible to deduce pollution conditions. This fuel cell stack involves the dedicated electrochemical cell being supplied with electrical power by the other electrochemical cells. Moreover, the measurement of pollution in the dedicated cell is not representative of the conditions in the rest of the electrochemical cells of the stack.

The invention aims to overcome one or more of these drawbacks. The invention thus pertains to a fuel cell stack such as defined in the appended claims.

The invention relates, moreover, to a method for manufacturing a fuel cell stack, such as defined in the appended claims.

Other features and advantages of the invention will become more clearly apparent from the description thereof that is provided below by way of completely non-limiting indication and with reference to the appended drawings, in which.

Figure 1:
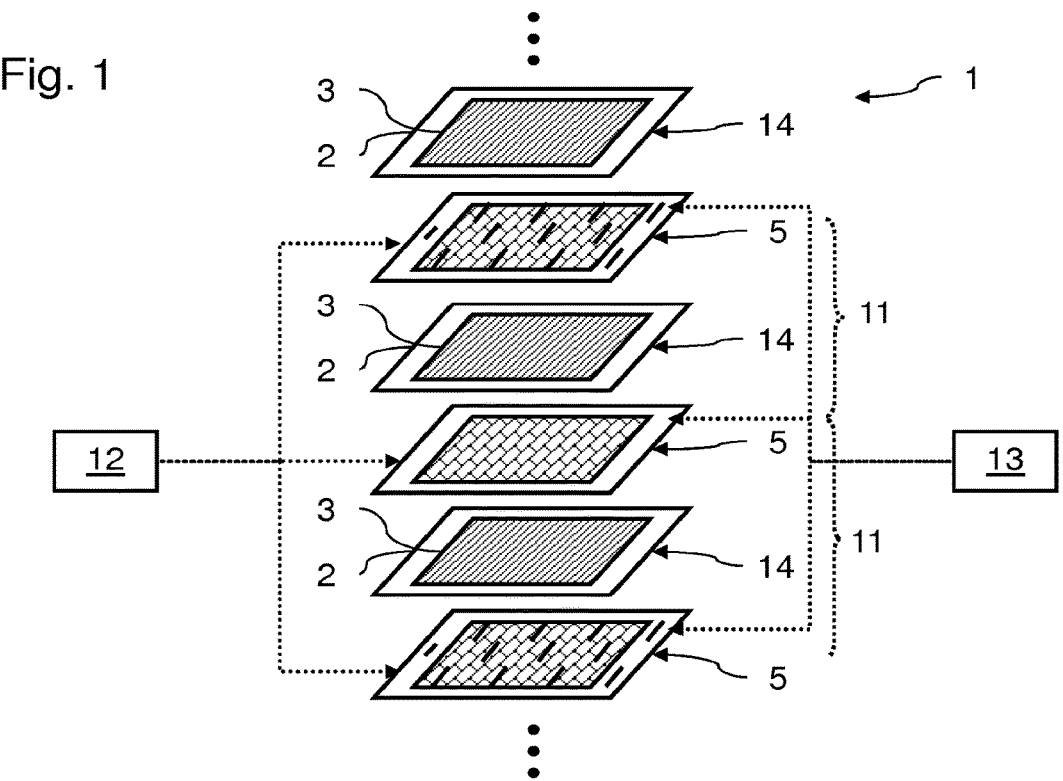
FIG. 1 is an exploded perspective view of an exemplary stack of membrane/electrode assemblies and bipolar plates for a fuel cell stack.

FIG. 1 is a schematic exploded perspective view of a stack of cells 11 of a fuel cell stack 1. The fuel cell stack 1 comprises multiple superposed cells 11. The cells 11 are of proton exchange membrane or polymer electrolyte membrane type.

The fuel cell stack 1 comprises a fuel source 12. The fuel source 12 here feeds dihydrogen into an input of each cell 11. The fuel cell stack 1 also comprises an oxidizer source 13. The oxidizer source 13 here feeds air into an input of each cell 11, the oxygen in the air being used as an oxidant. Each cell 11 also comprises exhaust channels. One or more cells 11 also have a cooling circuit.

Each cell 11 comprises a membrane/electrode assembly, or MEA, 14. A membrane/electrode assembly 14 comprises an electrolyte 2, a cathode (not illustrated) and an anode 3, which are placed on either side of the electrolyte and fixed to this electrolyte 2. The electrolyte layer 2 forms a semipermeable membrane allowing the conduction of protons while being impermeable to the gases present in the cell. The electrolyte layer also prevents electrons from passing between the anode 3 and the cathode.

A bipolar plate 5 is positioned between each pair of adjacent MEAs. Each bipolar plate 5 defines anodic flow channels and cathodic flow channels. Bipolar plates 5 also define channels for the flow of cooling liquid between two successive membrane/electrode assemblies.

In a manner known per se, during the operation of the fuel cell stack 1, air flows between an MEA and a bipolar plate 5, and dihydrogen flows between this MEA and another bipolar plate 5. At the anode, the dihydrogen is ionized in order to produce protons, which pass through the MEA. The electrons produced by this reaction are collected by a bipolar plate 5. The electrons produced are subsequently applied to an electrical load connected to the fuel cell stack 1 in order to form an electric current. At the cathode, oxygen is reduced and reacts with the protons in order to form water. The reactions at the anode and at the cathode are the following:

$H_2 \rightarrow 2H^+ + 2e^-$ at the anode;

$4H^+ + 4e^- + O_2 \rightarrow 2H_2O$ at the cathode.

During its operation, the fuel cell usually generates a continuous voltage between the anode and the cathode that is of the order of 1 V.

Figure 2:
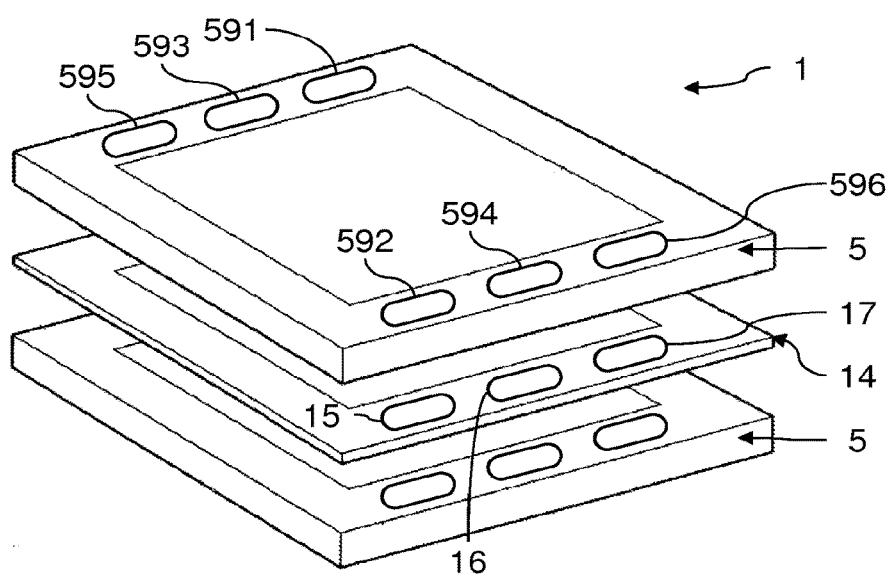
FIG. 2 is an exploded perspective view of bipolar plates and a membrane/electrode assembly that are intended to be stacked in order to form flow manifolds through the stack.

FIG. 2 is a schematic exploded perspective view of two bipolar plates 5 and a membrane/electrode assembly that are intended to be included in the fuel cell stack 1. The stack of the bipolar plates 5 and of the membrane/electrode assemblies 14 is intended to form a plurality of flow manifolds, the arrangement of which is illustrated here only schematically. For this purpose, respective apertures are made through the bipolar plates 5 and through the membrane/electrode assemblies 14. The bipolar plates 5 thus comprise apertures 591, 593 and 595 at a first end, and apertures 592, 594 and 596 at a second end opposite the first. The aperture 591 is used for example to form a fuel supply manifold, the aperture 596 is used for example to form a combustion residue discharge manifold, the aperture 595 is used for example to form a cooling liquid feed manifold, the aperture 592 is used for example to form a cooling liquid discharge manifold, the aperture 594 is used for example to form an oxidizer feed manifold and the aperture 593 is used for example to form a water discharge manifold.

The apertures of the bipolar plates 5 and membrane/electrode assemblies 14 are positioned facing one another in order to form the various flow manifolds. Apertures 15, 16 and 17 are for example made in reinforcements of the membrane/electrode assemblies 14 and are positioned facing the apertures 592, 594 and 596, respectively.

Figure 3:
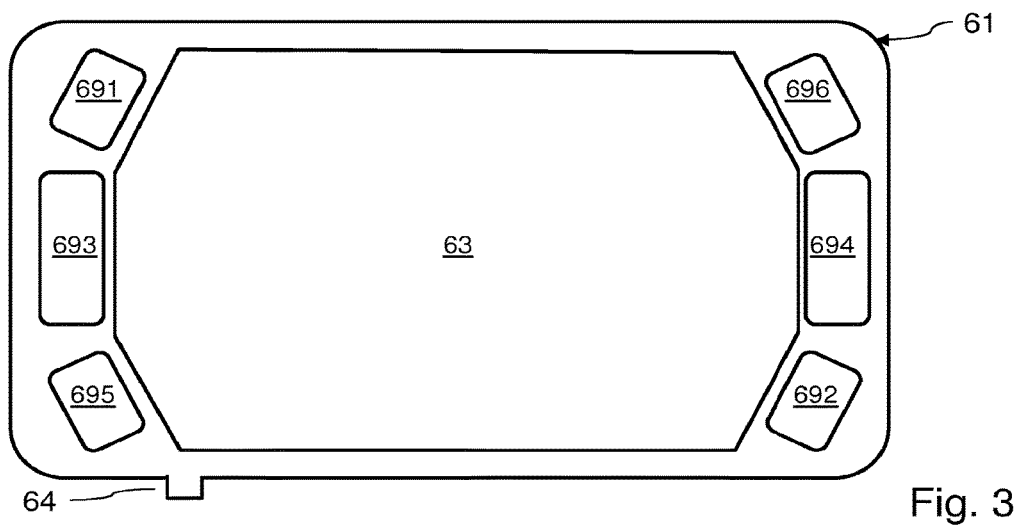
FIG. 3 is a view from above of a first reinforcement for a fuel cell according to one embodiment of the invention.

FIG. 3 is a view from above of a first type of reinforcement 61 for a fuel cell according to a first embodiment of the invention. The reinforcement 61 here takes the form of a perforated layer. The reinforcement 61 is for example made of a polymer material known per se. The reinforcement 61 comprises, in a manner known per se, a middle opening 63 intended to expose the majority of an electrode, the cathode in this instance. The reinforcement 61 furthermore surrounds this electrode. The reinforcement 61 furthermore comprises apertures 691, 693 and 695 that are made to one side of the middle opening 63. The apertures 691, 693 and 695 are intended to be positioned facing the apertures 591, 593 and 595 of the bipolar plates 5. The reinforcement 61 furthermore comprises apertures 692, 694 and 696 that are made on the side opposite the apertures 691, 693 and 695 with respect to the middle opening 63. The apertures 692, 694 and 696 are intended to be positioned facing the apertures 592, 594 and 596 of the bipolar plates 5. The reinforcement 61 comprises a protrusion 64 at one of its edges. The protrusion 64 is intended to form at least one surface that is not covered by another reinforcement 62, which will be described in detail below. The protrusion 64 is here positioned laterally with respect to the apertures 691 to 696.

Figure 4:
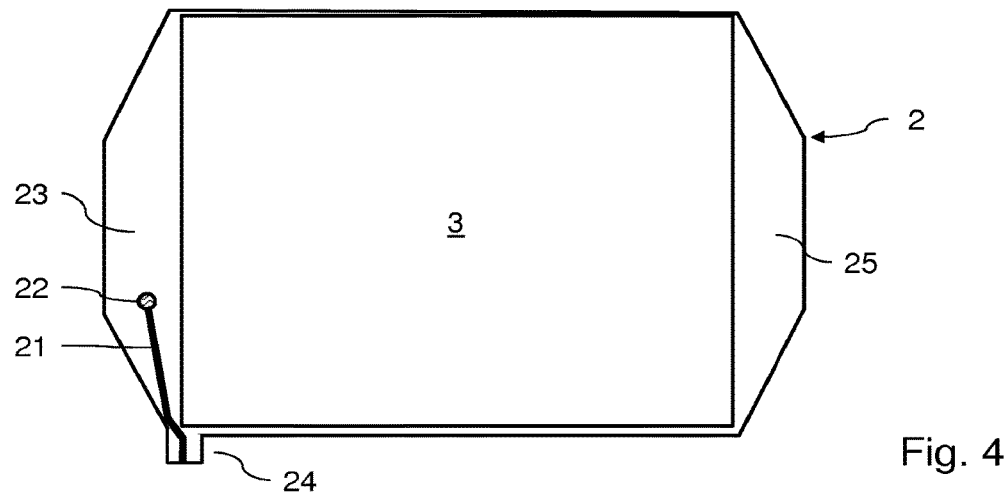
FIG. 4 is a view from above of a membrane and of an anode that are intended to be joined to the reinforcement of FIG. 3.

FIG. 4 is a view from above of a membrane 2 and an anode 3 that are intended to be joined to the reinforcement 61. The anode 3 is for example secured to the membrane 2.

Although not illustrated, a cathode is positioned against the membrane 2 on the side opposite the anode 3, and typically secured to the membrane 2.

The membrane 2 comprises an active zone and connection zones 23 and 25. The active zone corresponds to the portion of the membrane 2 that is covered by the anode 3 and plumb with the cathode. The connection zones 23 and 25 are positioned on either side of the anode 3 and are not covered by this anode 3. The connection zones 23 and 25 extend between respective flow manifolds and the anode 3. The connection zone 23 is here intended to be brought into contact with fuel arising from the fuel feed manifold, typically dihydrogen.

The membrane 2 additionally comprises a protrusion 24 at one of its edges. The protrusion 24 is here positioned in the lateral extension of the connection zone 23.

A conductive track 21 forms a circuit printed on the membrane 2, on the face bearing the anode 3 in the present case. The conductive track 21 here continuously extends from the connection zone 23 up to the protrusion 24. A measurement electrode 22 including a catalyst here makes contact with the membrane 2 in the connection zone 23. The electrode 22 is fixed here to the membrane 2 in the connection zone 23. As the electrode 22 is positioned in the connection zone 23, it is electrically insulated from the anode 3 by the membrane 2. The electrode 22 is thus not affected by the potential at the anode 3. The electrode 22 makes electrical contact with the conductive track 21.

The conductive track 21 is typically formed by depositing an ink on the membrane 2, this ink including a powdered conductive material mixed into an ionomer. Such a method for forming the conductive track 21 has been shown to be particularly advantageous for the obtention of a conductive track 21 of low thickness.

Figure 5:
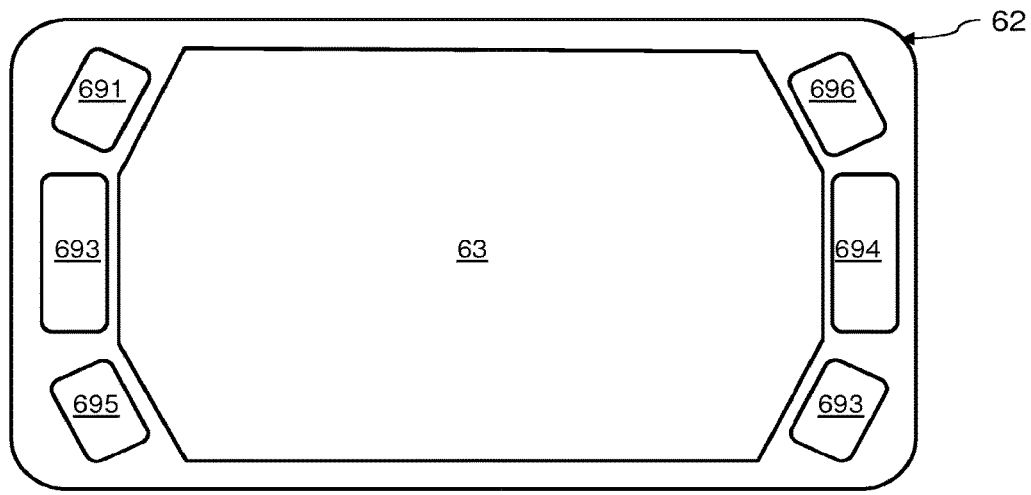
FIG. 5 is a view from above of a second reinforcement intended to be joined to the first reinforcement, and to the anode and membrane of FIG. 4, in order to form a membrane/electrode assembly.

FIG. 5 is a view from above of a second type of reinforcement 62 for the fuel cell according to the first embodiment of the invention. The geometry and the structure of the reinforcement 62 are substantially the same as those of the reinforcement 61. The reinforcement 62 differs from the reinforcement 61 only in the absence of a protrusion 64. In practice, by superposing the reinforcement 62 onto the reinforcement 61, the protrusion 64 remains exposed with respect to the reinforcement 62.

Figure 6:
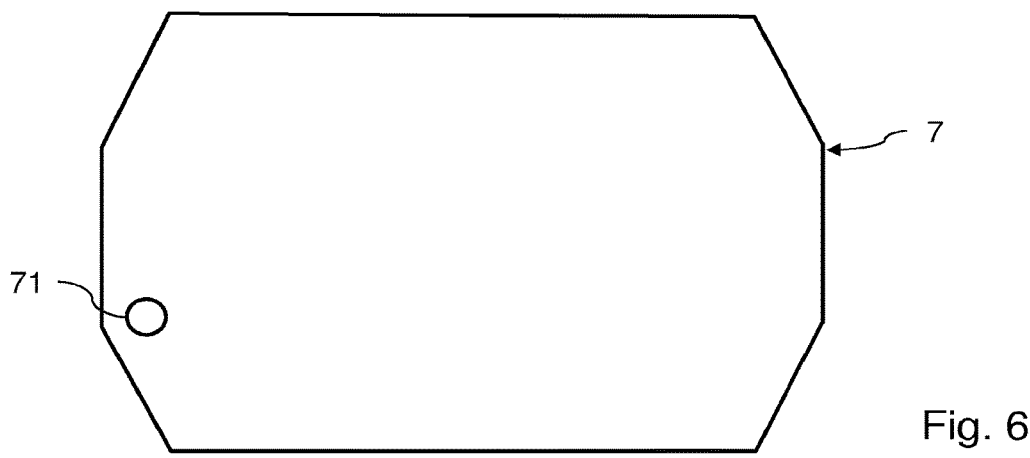
FIG. 6 is a view from above of a gas diffusion layer intended to be pressed flat against the anode of the membrane/electrode assembly of FIG. 4.

FIG. 6 is a view from above of a gas diffusion layer 7. The gas diffusion layer 7 is intended to be pressed flat into contact with the anode 3. The gas diffusion layer 7 comprises an aperture 71 (here a through-aperture). The aperture 71 comprises a contour that may include the contour of the electrode 22 with a certain spacing. Thus, the aperture 71 is intended to face the electrode 22, such that the electrode 22 does not make contact with the gas diffusion layer 7.

Figure 7:
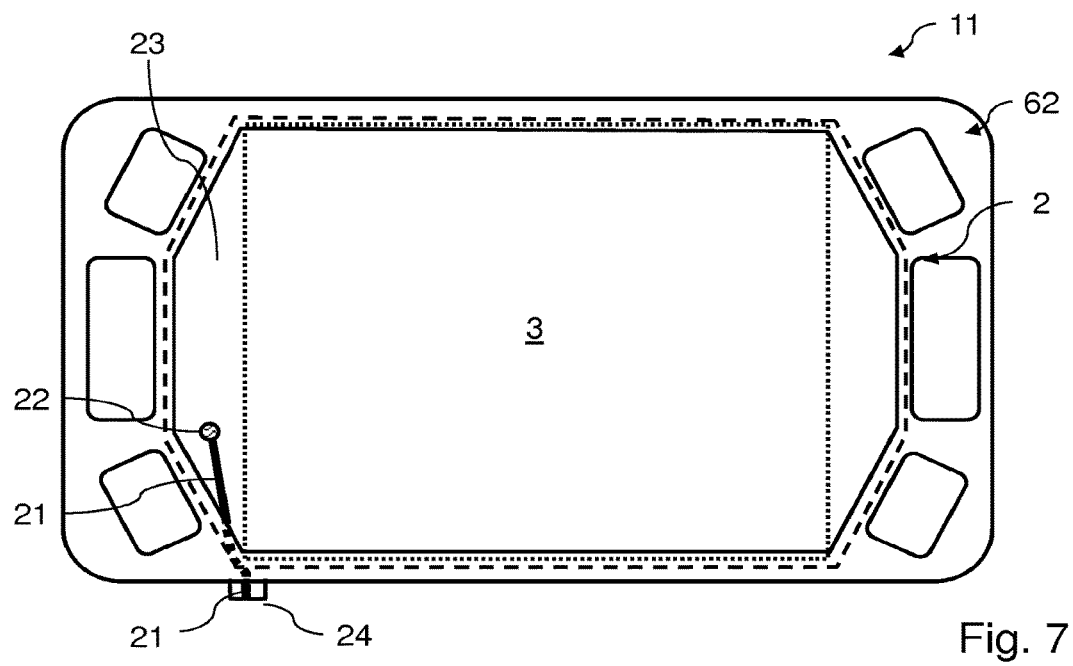
FIG. 7 is a view from above of an electrochemical cell during assembly.

FIG. 7 is a view from above of an electrochemical cell 11 during assembly. The reinforcement 61 surrounds the cathode and is fixed to the membrane 2. The middle aperture 63 of the reinforcement 61 thus exposes the cathode. A gas diffusion layer (not illustrated) may be positioned in contact with the cathode, through the middle aperture 63 of the reinforcement 61.

The reinforcement 62 is superposed onto the reinforcement 61. The reinforcement 62 surrounding the anode 3 is fixed to the membrane 2. The aperture 63 of the reinforcement 62 thus exposes the anode 3. The contour shown by a dashed line corresponds to the membrane 2 and the contour shown by a dotted line corresponds to the anode 3. The reinforcement 62 is here also fixed to the reinforcement 61.

The measurement electrode 22 is positioned in the connection zone 23 and is exposed by the middle aperture 63 of the reinforcement 62. The protrusion 24 (and the portion of the conductive track 21 borne thereby) protrudes beyond the reinforcement 62. The conductive track 21 therefore extends from the middle aperture 63 of the reinforcement 62 up to the outside of this reinforcement 62. A portion of the conductive track 21 may thus be connected to an external processing circuit. The external processing circuit (not described here) is configured to identify pollution in a flow according to the potential of the measurement electrode 22 delivered by the conductive track 21. The protrusion 64 of the reinforcement 61 is advantageously superposed onto the protrusion 24, so as to support this protrusion 24.

Figure 8:
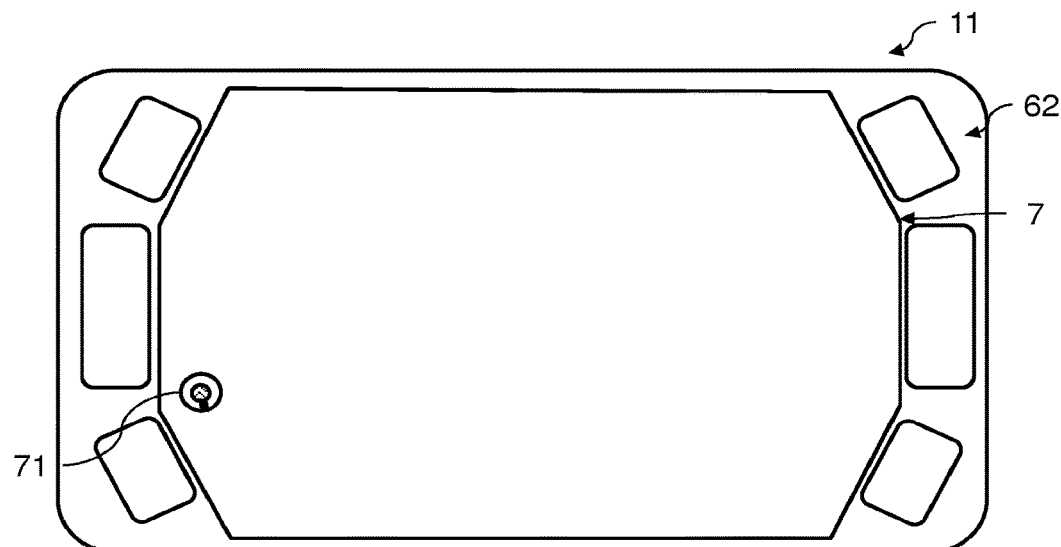
FIG. 8 is a view from above of the cell of FIG. 7 after the gas diffusion layer of FIG. 6 has been put in place.

FIG. 8 is a view from above of the electrochemical cell 11 in a later assembly step. The gas diffusion layer 7 of FIG. 6 is here brought into contact with the anode 3. The aperture 71 is here positioned facing the measurement electrode 22 such that the gas diffusion layer 7 and this measurement electrode 22 do not make contact.

It is also possible to envisage the measurement electrode 22 being formed after having added the gas diffusion layer 7, for example by depositing an ink through a through-aperture 71.

It is also possible to envisage the measurement electrode 22 being formed after having secured the membrane 2 to the reinforcement 62 but before having added the gas diffusion layer 7.

The inside of the aperture 71 may form electrical insulation between the measurement electrode 22 and the bipolar plate 5 that covers it. Advantageously, in order to guarantee that the measurement electrode 22 is electrically isolated with respect to a gas diffusion layer 7 or with respect to a bipolar plate 5, the measurement electrode 22 is covered by a porous, electrically insulating element (not illustrated). The porous element is for example formed from a microperforated polymer film.

Next, the stack obtained in FIG. 7, potentially supplemented with other components, is positioned between two bipolar plates 5. The bipolar plates 5 in particular compress the reinforcements 61 and 62. The added bipolar plates 5 are in particular configured so that at least one flow manifold passing therethrough is in communication with the anode 3 and the face of the membrane 2 to which the anode 3 is fixed. This flow manifold is thus in particular in communication with the connection zone 23. The protrusion 24 is for example configured so that it continues to laterally protrude with respect to the bipolar plates 5.

The thickness of the conductive track 21 is advantageously at most equal to 10 µm, and preferably at most equal to 5 µm, so that any increase in thickness where it passes below the reinforcement 62 is as small as possible. Such a conductive track 21, and in particular a track 21 produced in the form of a printed circuit, despite passing below the reinforcement 62, affects neither the quality of the seal of the stack nor the uniformity of the pressure exerted by the bipolar plates 5 on the reinforcements 61 and 62.

The conductive track 21 is here electrically insulated from the bipolar plate 5 above it by the reinforcement 62. The measurement electrode 22 is here electrically insulated from the bipolar plate 5 above it by the aperture 71 of the gas diffusion layer.

The bipolar plate 5 above the anode 3 may comprise a zone including homogenization channels. The zone of the homogenization channels is then made between the reactive flow channels above the anode 3 and a flow manifold. The zone of the homogenization channels is then advantageously superposed onto the connection zone 23 on which the measurement electrode 22 is formed.

The measurement electrode 22 advantageously comprises an ionomer matrix in which a catalytic material is included. The measurement electrode 22 advantageously comprises a catalytic material including platinum or a platinum alloy. Such a catalytic material has been shown to be suitable for example for detecting a carbon monoxide pollutant. The catalyst may advantageously be fixed to a carbon-based support. The measurement electrode 22 advantageously covers an area of between 5 and 40 $mm^2$ of the connection zone 23, so as to generate a measurement potential that is as reliable as possible. The measurement electrode 22 may advantageously be formed by depositing an ink in contact with the conductive track 21 and the membrane 2.

Figure 9:
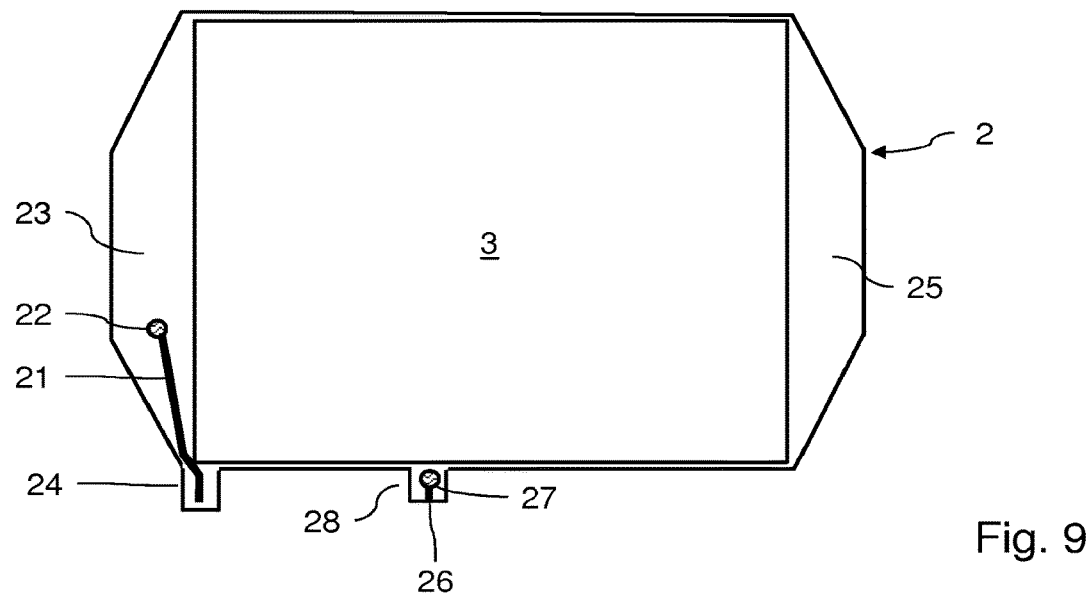
FIG. 9 is a view from above of a variant membrane associated with an anode.

Determining the pollution of a flow is advantageously achieved by comparing the potential of the measurement electrode 22 with a reference electrode. FIG. 9 illustrates a variant membrane 2 intended to facilitate the retrieval of a reference potential. In this variant, the membrane 2 comprises another protrusion 28, intended to protrude beyond the reinforcement 62. A conductive track 26 forms a printed circuit on the protrusion 28. This conductive track 26 is therefore positioned beyond the reinforcement 62. A reference electrode 27 is formed on the protrusion 28, making electrical contact with the conductive track 26. The fuel cell stack may then be configured to bring the electrode 27 into communication with a reference fluid, for example pure dihydrogen. The electrode 27 may thus deliver a reliable reference potential.

Although the described embodiment pertains to a measurement electrode in contact with an anodic dihydrogen flow, it is also possible to envisage:
- the measurement electrode being in contact with a flow of another type of fuel;
- the measurement electrode being in contact with a cathodic flow;
- the measurement electrode being in contact with a flow in a connection zone for connecting with an output manifold.

Although the described embodiment pertains to the detection of carbon monoxide in the flow, measurement electrodes with suitable catalysts could be used to detect other types of pollutants.

Although the illustrated embodiment includes a gas diffusion layer 7 equipped with an aperture facing the electrode 22, the fuel cell stack may be without a gas diffusion layer between the electrode 22 and the bipolar plate 5 superposed thereupon.

Although the illustrated embodiment includes a single measurement electrode in the connection zone, it is also possible to envisage another measurement electrode (associated with another conductive track) being positioned in this connection zone. It is possible to envisage these electrodes having different compositions. These electrodes may thus comprise one and the same catalytic material in different amounts or different catalytic materials. One electrode of the connection zone may for example be made of platinum while another electrode of the connection zone is made of PtRu.

It is also possible to envisage one measurement electrode being positioned at one connection zone and another measurement electrode (associated with another conductive track) at the connection zone positioned opposite with respect to the active zone.

The invention claimed is:

1. A fuel cell stack, comprising:
a membrane/electrode assembly including a proton exchange membrane, a first electrode forming an anode or a cathode making contact with a first face of the membrane, and a first reinforcement fixed to the first face of the membrane and surrounding the first electrode;
two bipolar plates between which the membrane/electrode assembly is positioned, at least one flow manifold passing through the bipolar plates and in communication with the first face of the membrane;
the first face of the membrane comprises an active zone, which is covered by the first electrode, and a connection zone, which is not covered by the electrode and is positioned between the flow manifold and the active zone;
the fuel cell stack further comprising:
a conductive track secured to the first face of the membrane and extending between the connection zone and an edge of the membrane protruding beyond the first reinforcement;
a measurement electrode including a catalytic material, positioned on the connection zone of the first face of the membrane and making electrical contact with the conductive track, the measurement electrode being electrically isolated with respect to the bipolar plates.

2. The fuel cell stack as claimed in claim 1, wherein thickness of the conductive track is at most equal to 10 µm.

3. The fuel cell stack as claimed in claim 1, wherein the conductive track is a circuit printed on the first face of the membrane.

4. The fuel cell stack as claimed in claim 1, wherein the measurement electrode is fixed in contact with the first face of the membrane.

5. The fuel cell stack as claimed in claim 1, wherein the measurement electrode comprises an ionomer matrix in which a catalytic material is included.

6. The fuel cell stack as claimed in claim 1, further comprising a gas diffusion layer making contact with the first electrode and one of the bipolar plates, the gas diffusion layer comprising an aperture facing the measurement electrode such that the gas diffusion layer and the measurement electrode do not make contact.

7. The fuel cell stack as claimed in claim 1, wherein the measurement electrode is covered by a porous, electrically insulating element.

8. The fuel cell stack as claimed in claim 1, wherein one of the bipolar plates comprises homogenization channels in communication with the flow manifold and superposed onto the connection zone.

9. The fuel cell stack as claimed in claim 1, further comprising a second reinforcement fixed to a second face of the membrane, the second reinforcement comprising a portion being superposed onto the edge of the membrane protruding beyond the first reinforcement.

10. The fuel cell stack as claimed in claim 1, wherein the catalytic material includes platinum or a platinum alloy.

11. The fuel cell stack as claimed in claim 1, wherein the measurement electrode covers an area of between 5 and 40 $mm^2$ of the connection zone.

12. The fuel cell stack as claimed in claim 1, wherein the first electrode is an anode.

13. The fuel cell stack as claimed in claim 1, further comprising a reference electrode and a second conductive track which is secured to the first face of the membrane, the reference electrode and the second conductive track being positioned on a portion of the membrane protruding beyond the first reinforcement, the reference electrode being positioned in contact with a reference fluid.

14. A method for manufacturing a fuel cell stack, comprising:
- producing a membrane/electrode assembly including a proton exchange membrane, a first electrode forming an anode or a cathode making contact with a first face of the membrane, and a reinforcement fixed to the first face of the membrane and surrounding the first electrode, the first face of the membrane comprising an active zone, which is covered by the first electrode, and a connection zone, which is not covered by the first electrode, the membrane/electrode assembly additionally comprising a conductive track secured to the first face of the membrane and extending between the connection zone and an edge of the membrane protruding beyond the reinforcement, the membrane/electrode assembly additionally comprising a measurement electrode including a catalytic material, positioned on the connection zone of the first face of the membrane and making electrical contact with the conductive track;
- positioning the produced membrane/electrode assembly between two bipolar plates, a flow manifold passing through the bipolar plates such that the flow manifold is in communication with the first face of the membrane and such that the measurement electrode is electrically isolated with respect to the bipolar plates.

15. The method for manufacturing a fuel cell stack as claimed in claim 14, comprising a prior forming the conductive track and securing the conductive track to the first face of the membrane by depositing an ink including a catalytic material on the first face of the membrane.

* * * * *